US008398539B2

(12) United States Patent
Stevens

(10) Patent No.: US 8,398,539 B2
(45) Date of Patent: Mar. 19, 2013

(54) PHALLUS DEVICE AND SYSTEM WITH SCREW ATTACHMENT

(76) Inventor: Charles Stevens, Chapel Hill, NC (US)

( * ) Notice: Subject to any disclaimer, the term of this patent is extended or adjusted under 35 U.S.C. 154(b) by 924 days.

(21) Appl. No.: 12/498,518

(22) Filed: Jul. 7, 2009

(65) Prior Publication Data

US 2011/0009691 A1 Jan. 13, 2011

(51) Int. Cl.
*A61F 5/00* (2006.01)

(52) U.S. Cl. .......................................................... 600/38

(58) Field of Classification Search ............... 600/38–41
See application file for complete search history.

(56) References Cited

U.S. PATENT DOCUMENTS

| | | | | |
|---|---|---|---|---|
| 4,722,327 | A * | 2/1988 | Harvey | 601/97 |
| 4,989,592 | A * | 2/1991 | Chang | 600/38 |
| 6,540,667 | B2 * | 4/2003 | Hickman | 600/38 |
| 6,547,717 | B1 * | 4/2003 | Green et al. | 600/38 |
| 6,849,041 | B2 | 2/2005 | Astin | |
| 6,991,599 | B2 * | 1/2006 | Hudson | 600/38 |
| 7,267,646 | B2 * | 9/2007 | Tucker | 600/38 |
| 7,452,326 | B2 * | 11/2008 | Fladl et al. | 600/38 |
| 2009/0131744 | A1 * | 5/2009 | Pattenden | 600/38 |

OTHER PUBLICATIONS

Ciba Specialty Chemicals, Plastic Additives, Ciba IRGAGUARD B 5000 Antimicrobial, Jul. 2001, US.

* cited by examiner

*Primary Examiner* — John Lacyk

(74) *Attorney, Agent, or Firm* — James G. Passé; Passé Intellectual Property, LLC

(57) ABSTRACT

The present invention is a phallus device and system for attaching a phallus to a mounting base. By utilizing a male/female screw attachment system a phallus can be attached to a number of different mounting bases such as a harness, a motorized device or the like. the particular advantage of the system is that the attachment is easy to achieve but less likely to come apart during use.

1 Claim, 4 Drawing Sheets

PHALLUS DEVICE AND SYSTEM WITH SCREW ATTACHMENT

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to the attachment of a phallus device. In particular the present invention relates to a phallus device and system comprising a screw attachment for facilitating attachment and removal to different substrates.

2. Description of Related Art

The design and use of phallus shaped devices for use as a sexual aid are well known. Devices are normally hand held or attached to a substrate such as another person or a fixed object during uses. Such sexual aids are designed to enhance, be a substitute for or in addition to the male phallus. They can be used as a prosthetic on both males and females. A wide variety of shapes are known with phallus type devices from the very realistic looking to the general phallus shape, to shapes with additional surface treatments or shapes such that do not resemble a simple phallus.

Frequently, the phallus is mounted on a harness, a strap, a wall or table mounting depending on the particular use or person using the device. Removable and interchangeable mounting methods allow the user to attach a variety of different shaped phalluses for different purposes, variety and enjoyment. Frequently the attachment means, while simple to use, creates a problem of keeping the phallus attached during use as a sexual aid. It is clear that attachment means that are easy to use, yet retains a phallus in a comfortable and effective means for the user, achieves a number of advantages of the current art.

BRIEF SUMMARY OF THE INVENTION

The present invention relates to the discovery that if a female or male threaded attachment means is used on a phallus then the attachment is stronger than the prior art, the attachment is easy to use and is less likely to accidently become detached. The base unit to be used with the phallus comprises the corresponding male or female threaded portion for attaching the phallus to the base.

DETAILED DESCRIPTION OF THE INVENTION

Figure 1:
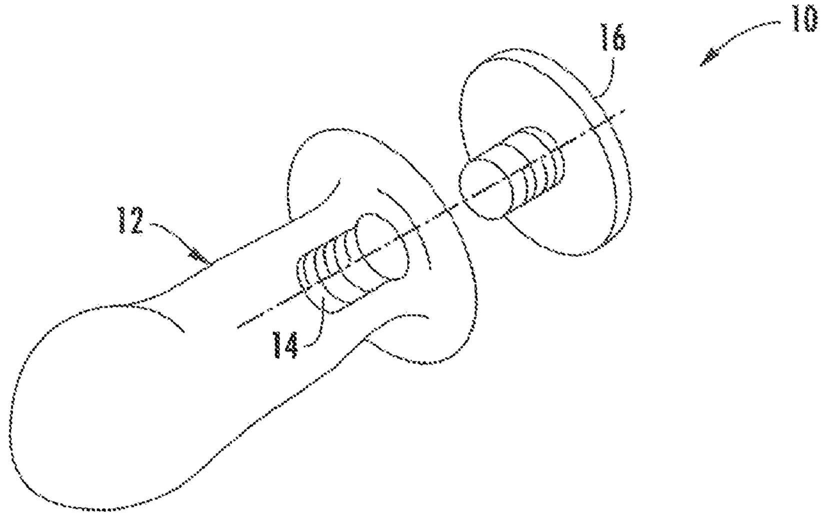
FIG. 1 is a perspective transparent view of an embodiment of the invention depicting a female attachment bore with a male threaded mounting base.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein a "phallus device" is any shaped device that can be used as a sexual stimulation aid. Typically, phalluses are elongated shafts replicating in detail or in simple fashion the male sexual organ. However, additional surfaces and other shapes such as an egg shape, round shape or the like, have been used for phallus devices and such shapes used for sexual stimulation are intended herein.

Phallus devices are usually made of material compatible with the individual user of the device. Typical materials that can be used to construct a phallus device of the present invention include polymers, such as silicone and can include both elastomeric materials as well as non-elastomeric materials. Other materials, such as blunted metals or the like, can also be used but the final selection of material needs to be such that it supports the attachment method of the present invention.

Such selection of materials is within the skill in the art in view of the disclosure of the present invention.

The phallus device of the present invention comprises an attachment screw. As used herein an "attachment screw" refers to either inner female threading in the inside of the phallus device or an exterior shaft having male threading. The threading is of the type designed to couple or attach to corresponding threaded coupling, i.e. male couple to female coupling. In use, the phallus device is mounted on the matching mounting screw base. In other embodiments, the phallus device is used alone as an aid but can be used at other times with a mounting base. In the case where the attachment screw is a female threaded coupling, other devices can be inserted into the cavity for other sexual aid purposes. In this case, the inserted device would not have a threaded matching mounting. An example of such insertion would be a vibratory device such as a tapered egg or the like. One skilled in the art could envision other devices for use within the cavity of the phallus. It is clear that another advantage of the present invention is not only that it can be used with a mounting base, but it can also be used with a variety of other devices for use as an aid, even if it is not always used with the mounting base of the present invention.

The thread of the attachment screw and mounting base used herein are designed to mate together and in one embodiment such that the male and female screws when mated mate with essentially no extra thread. The thread of the screws can be designed based on the individual material used, the strength of the connection needed and the like, however, one skilled in the art could easily optimize the screw thread size, the diameter of the screw shaft and the length of the shaft in view of the present invention without undue experimentation. The length or depth of the attachment screw is one of choice of the user. Clearly a female attachment screw is limited by the depth of the material the female screw is mounted into. In one embodiment, the length of the attachment screw is from about 1 to 2 inches and in another it is from about 1 to 1.25 inches in length. The diameter can, in one embodiment, be from about ½ inch to about 1.25 inches in diameter Typical manufacturing methods for phallus type devices are molding, shaping, casting and the like and are within the skill in the art.

As used herein, the phrase "mounting base" refers to a device and system having a threaded portion designed to mate with the attachment screw of the phallus invention. Therefore, where the phallus has female threading, the mounting base would have male threading. The interchangeability of male and female threading will give the designer of the particular device latitude in designing a device differently depending on the base unit and the exact type of usage. Examples of base units include, but are not limited to, a dildo harness such as designed to be worn around the waist area of an individual who will operate the phallus. Another embodiment of the mounting base is a threaded rod unit mounted on a drive unit of a mechanical thrusting type machine. In using thrusting machines it is especially difficult to keep a phallus in place during use and prior art attempts have included high pressure hose clamps which require a bolt driver and quite a bit of torque to firmly attach a phallus. The attachment means of the present invention allows hand mounting without the need to worry that the phallus will become detached during use. Another embodiment of the mounting base is a phallus with a handle. By attaching a handle to the mounting base, the user can manually use the phallus device assured that a firm grip can be maintained on the phallus until the user is finished using the device.

In another embodiment of a mounting base, there is included a base having an inner female screw thread separately from the attachment couple for the phallus. With this embodiment the base can be attached to a surface and the base attached firmly by use of a matching screw retaining knob which screws into the base from the opposite side of the wall, thus, firmly and removably attaching the phallus mounting base to the wall for the purpose of mounting the phallus on that spot on the wall.

In use it is a simple matter of taking a matching phallus and the mounting base and then screwing them together. The phallus can be screwed onto or into the base or vice-versa depending on the particular design of the system or the particular use. If the phallus needs to be aligned in a particular orientation on the base then one skilled in the art can match the threads in such a manner that the phallus arrives at the right position each time it is attached to the mounting base by making sure the length of the two mating attachment screws achieves that result.

Now referring to the drawings, FIG. 1 is a perspective transparent view of a phallus and mounting base of the invention. The phallus system 10 comprises a phallus shaped shaft 12 that has a female inner thread 14 attachment screw. As can be seen mounting base 16 can attach via the female inner threads 14 of the phallus. One can easily reverse the male/female threading in view of this drawing.

Figure 2:
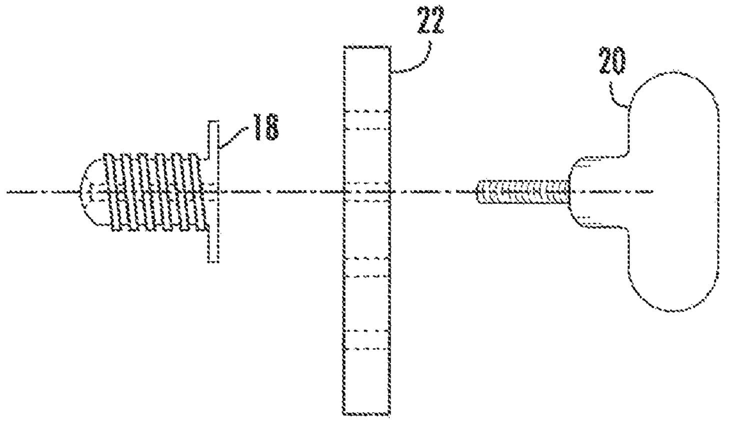
FIG. 2 is a side view of a mounting base and knob retaining mechanism.
Figure 3A:
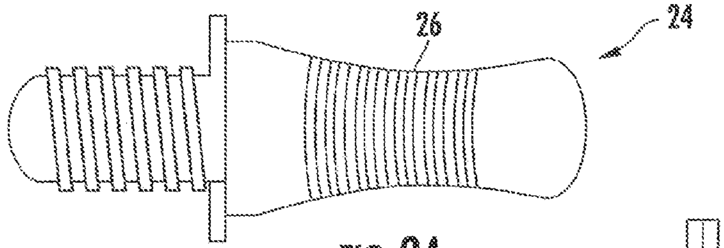
FIGS. 3*a*-3*d* depict side views of a number mounting bases.
Figure 3B:
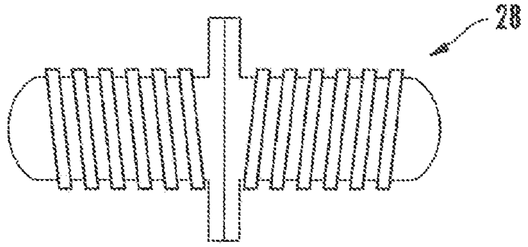
Figure 3C:
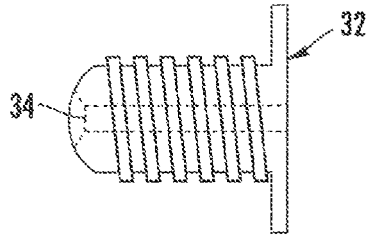
Figure 3D:
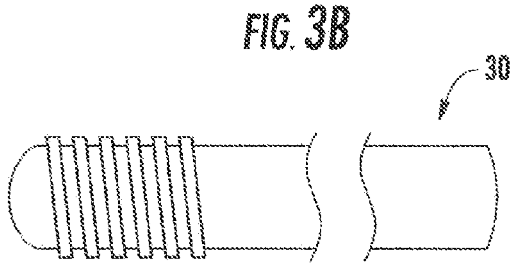

In FIG. 2 there is shown a mounting base 18 which is capable of attaching to pegboard 22. The mounting base 18 is placed up against the peg board and screw knob retaining mechanism 20 is screwed through the peg board 22 and into base 18.

In FIG. 3*a*-3*d* there are male attachment screws depicted for both the phallus and base. Phallus 24 having male threaded attachment screw also has ribbing 26. Mounting base 28 has two mounting bases so that two opposing phallus may be attached together. Mounting base 32 shows the female threaded core 34 for use with the knob mechanism of FIG. 2 and phallus 30 depicts a handle mounting base for attaching a phallus.

Figure 4:
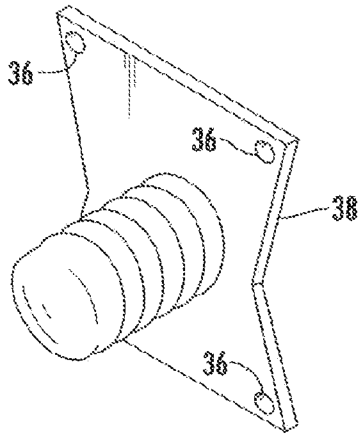
FIG. 4 is a perspective view of a mounting base design to be used with a harness or flat object mounting.

FIG. 4 depicts mounting base 38 in a perspective view. This mounting base 38 is designed to be used with a harness or used otherwise by using straps, ropes, nails or the like through mounting holes 36 which can be used to attach base 38 to another device or substrate.

Figure 5:
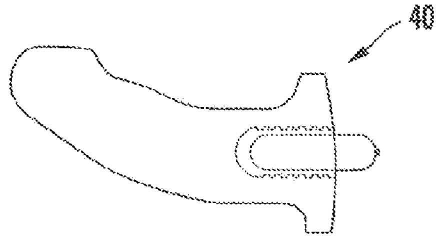
FIG. 5 is a side view of the phallus with a vibratory device mounted in the female threaded portion of the phallus.

FIG. 5 depicts a phallus 40 with a female threaded coupling. In this side view a vibratory device is depicted as positioned and placed into the female threaded coupling cavity.

Figure 6A:
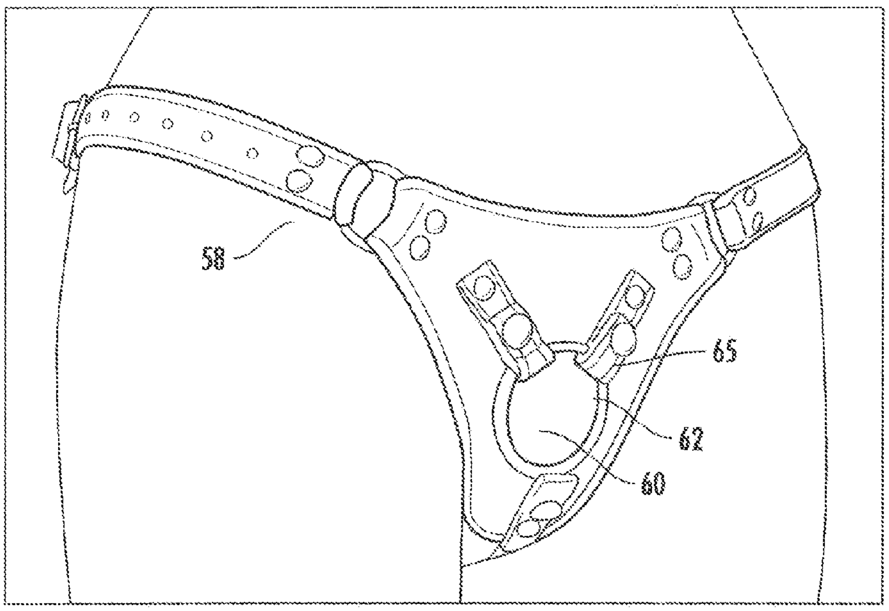
FIG. 6*a* is a perspective view of a standard O ring harness.
Figure 6B:
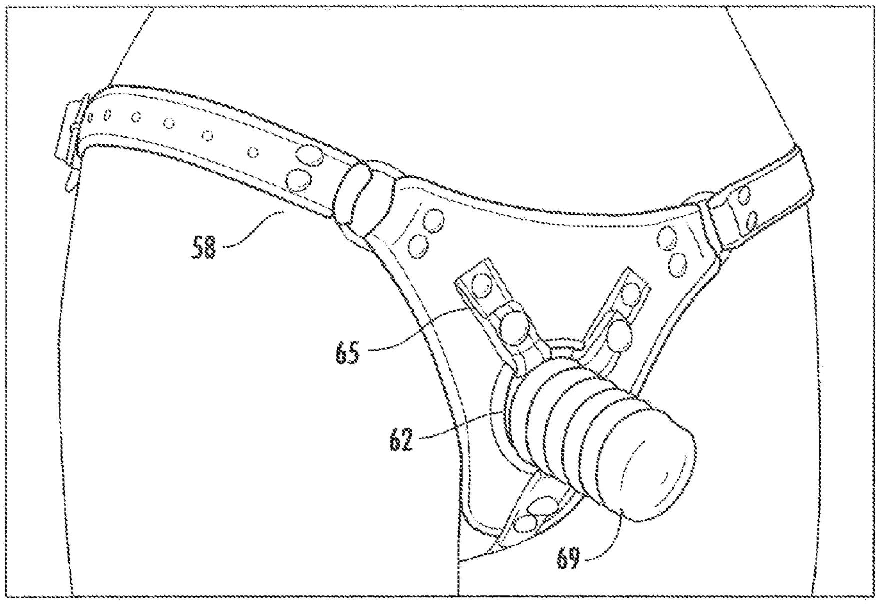
FIG. 6*b* is a perspective view of the standard O ring harness with a male screw mount attached.

FIG. 6*a* shows a perspective view of a standard O ring harness. The strap 58 has toy mounting hole 60. The hole 60 is fitted with O ring 62 held in place by straps 65. Standard toys fitted with the matching adaptor fit in hole 60 and held in place by O ring 62. FIG. 6*b* shows a perspective view of harness 58 that has a screw adaptor 69 which fits in the hole of the harness 58. With the screw adaptor 69 in place, a phallus device depicted in FIG. 1 could be used with the standard harness. Thus, someone who had a variety of different types of dildos could choose one harness and use the devices of the present invention with them.

The above examples and drawings are not intended to be limiting variations of the present invention. Various materials, designs, shapes and the like are within the scope of the present invention and as such the claims which follow should not otherwise be limited.

What is claimed is:

1. A phallus system comprising:

a) a phallus device comprising:

an attachment screw selected from the group consisting of an inner female threaded coupling or an outer male threaded coupling; and b) a mounting base having a threaded portion designed to mate with the attachment screw of the phallus c) an O ring harness with a toy mounting hole the mounting base adapted to fit through the toy mounting hole and be held in place with the O ring such that the phallus device can be screwed to the mounting base.

* * * * *